United States Patent [19]

De Vries

[11] 4,417,573
[45] Nov. 29, 1983

[54] PATIENT ADAPTOR FOR MEDICAL VENTILATOR

[75] Inventor: Douglas F. De Vries, Redlands, Calif.

[73] Assignee: Bear Medical Systems, Inc., Riverside, Calif.

[21] Appl. No.: 279,957

[22] Filed: Jul. 2, 1981

[51] Int. Cl.³ ............................................. A61M 16/00
[52] U.S. Cl. ............................ 128/204.25; 128/205.24
[58] Field of Search .................... 128/204.21, 204.25, 128/204.26, 205.24

[56] References Cited

U.S. PATENT DOCUMENTS

| | | | |
|---|---|---|---|
| 2,376,348 | 5/1945 | Fox | 128/29 |
| 2,408,136 | 9/1946 | Fox | 128/29 |
| 3,039,481 | 6/1962 | Schreiber et al. | 128/204.19 |
| 3,073,298 | 1/1963 | Stanton | 128/29 |
| 3,385,295 | 5/1968 | Beasley | 128/145.8 |
| 3,441,041 | 4/1969 | Schreiber | 128/204.25 |
| 3,465,752 | 9/1969 | Brychta et al. | 128/145.8 |
| 3,485,243 | 12/1969 | Bird et al. | 128/145.8 |
| 3,621,842 | 11/1971 | Manley | 128/145.6 |
| 3,769,973 | 11/1973 | Esbenshade, Jr. | 128/145.8 |
| 3,842,828 | 10/1974 | Bird | 128/145.8 |
| 3,859,995 | 1/1975 | Colston | 128/145.8 |
| 3,881,486 | 5/1975 | La Sourcade | 128/145.8 |
| 3,903,881 | 9/1975 | Weigl | 128/145.6 |
| 4,082,093 | 4/1978 | Fry et al. | 128/142.2 |

Primary Examiner—Henry J. Recla
Assistant Examiner—Karin M. Reichle
Attorney, Agent, or Firm—Howard J. Klein

[57] ABSTRACT

A patient adaptor fitting for a medical ventilator includes a jet pump having a nozzle receiving breathing gas from the inspiratory leg of the patient circuit, and a throat in communication with the expiratory leg of the patient circuit. Gas flows from the nozzle to the throat through a chamber in communication with the patient's breathing passages. The nozzle and the throat are dimensioned so as to produce a pressure drop in the chamber which balances the pressure drop through the expiratory leg of the patient circuit, thereby minimizing residual positive end expiratory pressure (PEEP) caused by the pneumatic resistance in the expiratory leg. The throat and nozzle dimensions are also selected so that the minimization of the residual PEEP occurs over a relatively wide range of flow rates into the nozzle.

1 Claim, 4 Drawing Figures

U.S. Patent  Nov. 29, 1983  4,417,573
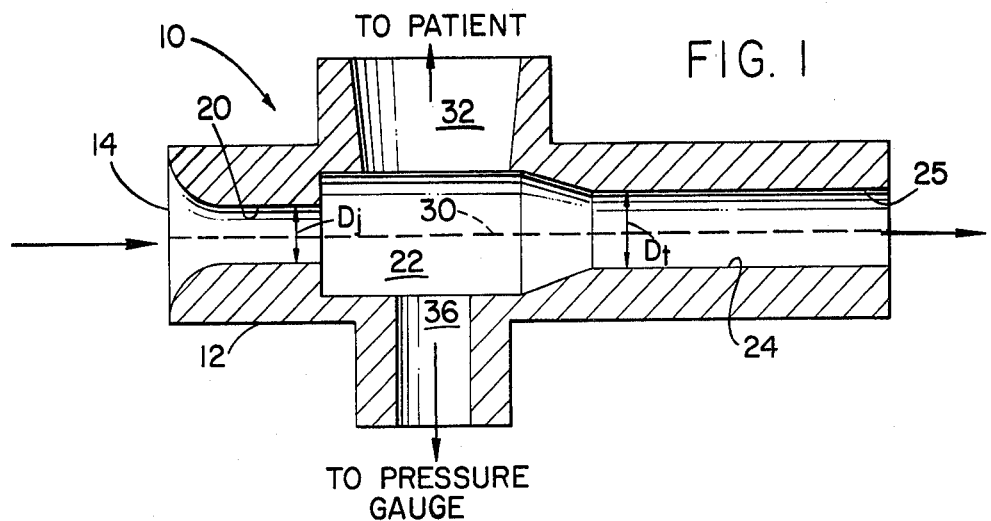
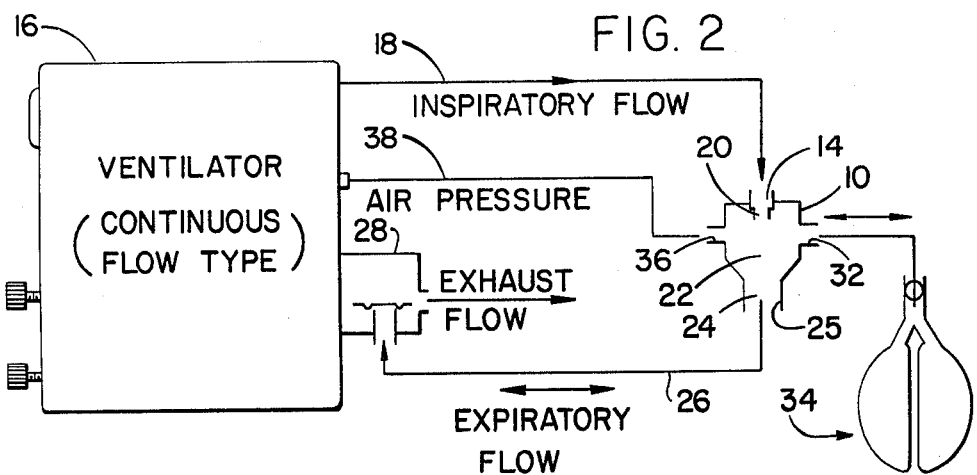
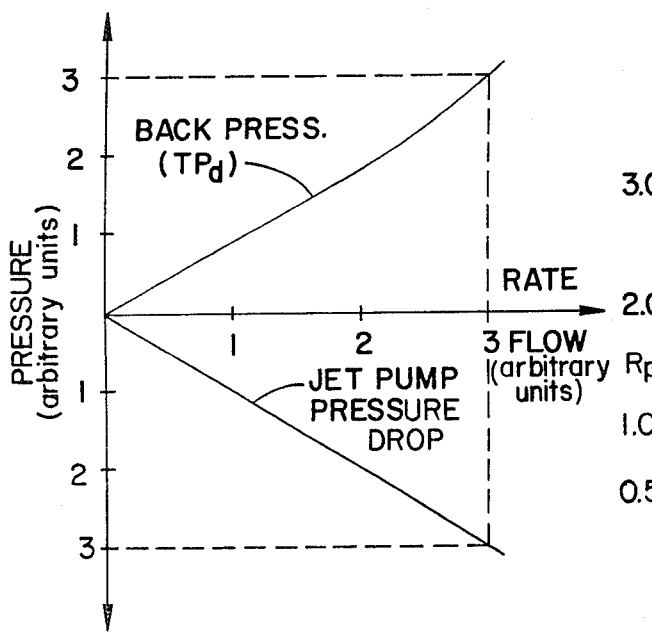
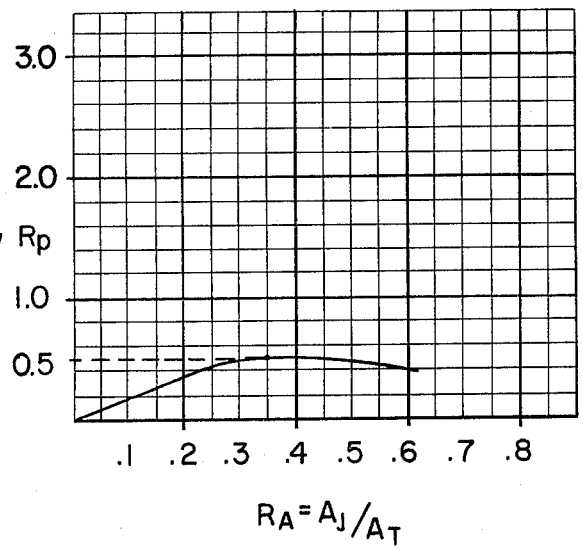

PATIENT ADAPTOR FOR MEDICAL VENTILATOR

BACKGROUND OF THE INVENTION

Medical ventilators, of the type providing a continuous gas flow, are widely used. In such ventilators, breathing gas flows continuously or nearly continuously, through a patient circuit having an inspiratory leg and an expiratory leg, coupled by a fitting or patient adaptor, which is in communication with the patient's breathing passages. This adaptor is commonly referred to as a "tee" or a "wye," depending upon its particular configuration. Thus, the patient, breathing through the adaptor, receives gas from the inspiratory leg during inhalation, and exhales through the adaptor into the expiratory leg during exhalation.

The expiratory leg commonly has an exhalation valve which is open only during exhalation. Thus, during inhalation, gas flows only to the patient. At the end of the inspiratory phase of the patient's respiration, the exhalation valve opens, allowing gas to flow from the patient, through the exhalation valve, and out the exhaust port of the ventilator. During exhalation, gas continues to flow from the inspiratory leg to the expiratory leg through the patient adaptor. This latter flow continues in this manner until the start of the next inhalation phase.

An undesirable characteristic of such a system is that the pressure at the patient adaptor is always slightly higher than the ambient pressure (at the exhaust port), even after exhalation is complete. Thus, the patient will experience a residual positive end expiratory pressure, which is referred to as "inadvertent PEEP." Although a number of factors contribute to inadvertent or residual PEEP, the dominant factor is usually the pressure drop that the gas undergoes as it passes through the expiratory leg due to the pneumatic resistance of the expiratory leg components, including the exhalation valve.

While there are therapeutic regimens which require some degree of PEEP, in many cases PEEP is not desired. Moreover, in those cases where PEEP is desired, the requirement is to control the degree of PEEP carefully. Thus, inadvertent PEEP can not only impair the ability to operate without PEEP, but it can also make difficult the achievement of a precisely-controlled PEEP.

Although conventional pressure-compensating means can be used to minimize inadvertent PEEP, such means are effective only for relatively narrow ranges of ventilator operational parameters, e.g., flow rate and expiratory leg pneumatic resistance. This is due to the variation in inadvertent PEEP which results from variations in these machine characteristics. Thus, for a given patient, inadvertent PEEP will vary proportionately with ventilator flow rate or expiratory leg pneumatic resistance.

It has long been known that the exhalation phase of respiration can be aided or assisted by the use of a venturi jet pump in the patient circuit. Typically, the jet pump is used to create a negative pressure at the patient connection so that gas is extracted from the patient's lungs. See, for example, U.S. Pat. Nos. 3,465,752—Brychta et al.; 2,408,136—Fox; 2,376,348—Fox; 3,073,298—Stanton; and 3,485,243—Bird et al. However, none of the devices disclosed in these patents addresses the problem of minimizing inadvertent PEEP over a wide range of flow rates in a continuous flow ventilator system.

This problem has been addressed using a system such as that disclosed in U.S. Pat. No. 3,842,828—Bird. This system employs a venturi jet pump in the expiratory leg of the patient circuit, between the patient adaptor and the exhalation valve. The gas provided to the nozzle of the jet pump is supplied separately from the gas in the patient circuit, and thus has no inherent relationship to the gas flow rate in the patient circuit. Accordingly, adjustment of the negative pressure provided by the jet pump to compensate for variations in inadvertent PEEP due to changes in patient circuit flow rate is effected by varying the flow rate of the gas supplied to the jet pump nozzle by means of a manually-activated flow rate control valve.

From the foregoing, it can be appreciated that the ventilator art would benefit from a mechanism which minimizes inadvertent PEEP over a wide range of patient circuit flow rates, and which does so without the need for a separate pneumatic circuit having its own controls which must be monitored and manually adjusted. Moreover, it would also be beneficial to provide a mechanism which achieves such operational goals, while also being simple to construct and use, and which is also easily adaptable to widely varying operational characteristics.

SUMMARY OF THE INVENTION

Broadly, the present invention comprises a ventilator patient adaptor, for example a "tee" adaptor, which incorporates an integral venturi jet pump. The jet pump has a nozzle receiving the inspiratory gas flow from the ventilator and a throat in communication with the expiratory leg of the patient gas circuit. Between the nozzle and the throat is a chamber in communication with the patient's air passages through a patient connection port. Inspiratory gas experiences an acceleration in flow rate as it passes through the nozzle, and, upon entry into the chamber, exercises a reduction in pressure at the patient connection port. (The processes by which this phenomenon is manifested are well-known. See, for example, Kroll, "The Design of Jet Pumps," *Chemical Engineering Progress*, Vol. 1, No. 2, February 1947, pp. 21-24).

During inhalation, an exhalation valve in the expiratory leg of the patient circuit is closed. Accordingly, inspiratory gas flows to the patient through the patient connection port. When exhalation begins, however, the exhalation valve opens, and inspiratory gas flows from the nozzle, through the jet pump throat, and into the expiratory leg, exiting through the exhalation valve to the ambient atmosphere. The reduction in pressure at the patient connection port induced by the accelerated gas flow from the nozzle will then offset, at least in part, the pneumatic back-pressure experienced at the jet pump throat as a result of the pneumatic resistance of the expiratory leg, which back-pressure manifests itself, to the patient, as residual, or "inadvertent," positive end expiratory pressure (PEEP). By properly selecting the dimensions of the jet pump components, and particularly the nozzle and throat diameters, the pressure drop at the patient connection port can be made to offset completely the expiratory leg generated back-pressure, so that the next pressure at the patient connection port is substantially at ambient pressure. Thus, the patient "feels" ambient pressure upon exhalation, so that inadvertent PEEP is minimized to very low levels or even completely eliminated. Moreover, since the back pressure generated by the expiratory leg, and the patient connection port pressure drop generated by the jet pump are both approximately proportional to the inspiratory gas flow rate, the result of minimizing or eliminating inadvertent PEEP by balancing the back-pressure with the jet pump-induced pressure drop will obtain over a wide flow rate range.

From the foregoing, it can be seen that the present invention achieves the desired objectives of minimizing inadvertent PEEP over a wide range of patient circuit gas flow rates without the need for a pneumatic circuit separate from the patient circuit. Moreover, it can be seen that the invention self-compensates for varying flow rates, without the need for pneumatic controls. As will be shown in more detail below, the invention is of a simple construction which lends itself to economy of manufacture. In addition, it can be easily connected to and disconnected from the ventilator. Thus, a variety of patient adaptors having jet pumps of different operational dimensions can be kept on hand to accommodate ventilators with differing inspiratory flow pressures and expiratory leg pneumatic resistances.

BRIEF DESCRIPTION OF THE DRAWINGS

FIG. 1 is a cross-sectional view of the preferred embodiment of a patient adaptor in accordance with the present invention;

FIG. 2 is a diagrammatic representation of a continuous flow ventilator connected to a patient with a patient adaptor of the type shown in FIG. 1;

FIG. 3 is a graph showing back pressure at the adaptor outlet and the jet pump-induced pressure drop versus flow rate through the adaptor, all in arbitrary units; and FIG. 4 is a graph illustrating an empirically-derived relationship between several physical parameters used in calculating an optimal ratio of jet pump nozzle diameter to jet pump throat diameter for the adaptor of FIG. 1.

DETAILED DESCRIPTION OF THE PREFERRED EMBODIMENT

Referring to FIGS. 1 and 2, a patient "tee" adaptor 10 is illustrated. As shown, the adaptor 10 has a body 12 having an inlet 14 for receiving an inspiratory gas flow from a ventilator 16 through the inspiratory leg of the patient pneumatic circuit, said inspiratory leg being represented in FIG. 2 by line 18.

The inlet 14 tapers down, in a manner well known in the art, to a constricted jet nozzle 20 having a diameter $D_j$. The nozzle 20 communicates with an enlarged-diameter chamber 22, which, in turn, tapers down to enter a throat 24, of substantially constant diameter $D_t$. The throat 24 has an outlet 25 which is fluidly connected to the expiratory leg of the patient circuit, represented in FIG. 2 by line 26. As shown in FIG. 2, the expiratory gas flow eventually is exhausted to the atmosphere through an exhalation valve 28.

As seen in FIG. 1, the nozzle 20 and the throat 24 are coaxial along longitudinal axis 30, standard practice in the construction of jet pumps. Entering the chamber 22 substantially perpendicularly to the axis 30 is a patient connection port 32, which is fluidly coupled to the patient's air passages (represented schematically in FIG. 2 at 34) by suitable conventional means wellknown in the art. It is advantageous to provide a patient pressure sampling port 36 in communication with the chamber 22. The patient pressure sampling port 36 can be coupled, as by line 38 (FIG. 2) to a pressure gauge, or the like (not shown) in the ventilator 16.

In operation, gas is continuously, or nearly continuously, delivered from the ventilator to the nozzle inlet 14 via the inspiratory flow line 18. During the inhalation phase of the patient's respiratory cycle, the exhalation valve 28 is closed, thereby effectively closing the expiratory flow line 26, and causing gas to be directed to the patient via the chamber 22 and the patient connection port 32. At the onset of the patient's exhalation, the exhalation valve 28 is opened (by conventional means, not shown), and gas flows through the throat 24, the expiratory flow line 26, and the exhalation valve 28 to atmosphere (ambient pressure). Since the ventilator 16 is of the continuous flow type, the gas flowing through the expiratory leg of the patient circuit is received from the inspiratory flow line 18, via the nozzle 20, as well as from the patient, via the patient connection port 32.

Because of the pneumatic resistance of the expiratory flow line 26 and the exhalation valve 28, a back pressure is developed at the outlet 25 of the throat 24. In other words, the pressure at the throat outlet is elevated above ambient by an amount $TP_d$ which is a function of the flow rate and the pneumatic resistance offered by expiratory leg of the patient circuit. (For a given expiratory leg configuration, the value of $TP_d$ may be considered an essentially linear function of flow rates for gas flows that are not highly turbulent.) In the absence of the jet nozzle 20, this back pressure $TP_d$ would be transmitted to the patient, via the chamber 22 and the patient connection port 32, so that the patient would exhale against the pressure $TP_d$, rather than to ambient pressure. The result would be that, at the end of exhalation, the patient would "feel" the pressure $TP_d$ as a residual, or inadvertent, positive end expiratory pressure (PEEP).

However, due to physical processes well-known in the field of pneumatics, the accelerating gas flow through the jet nozzle 20 causes a reduction in pressure in the chamber 22 from the nozzle 20. This pressure drop, which is a function of the jet pump geometry and the gas flow rate therethrough, tends to offset the back pressure $TP_d$. It will thus be appreciated that if the pressure drop in the chamber 22 effected by the jet pump is equal in magnitude to $TP_d$, the net pressure in the chamber will be substantially zero PEEP. The goal, therefore, is to design the jet pump geometry to balance, as closely as possible, the back pressure $TP_d$ with the jet pump-induced pressure drop to minimize or eliminate inadvertent PEEP.

As shown graphically in FIG. 3, both the back pressure ($TP_d$) produced by expiratory leg pneumatic resistance, and the pressure drop effected by the jet pump are substantially linear functions of flow rate. In FIG. 3, the curves for both $TP_d$ and the jet pump-induced pressure drop have been drawn to indicate the optimal relationship therebetween as produced by the present invention. That is, for any given flow rate, the jet pump pressure drop is substantially equal in magnitude, but opposite in sign, to the back pressure $TP_d$.

As previously mentioned, the result illustrated in FIG. 3 is largely a function of the geometry of the jet pump. As is known in the art of jet pump design, among the factors affecting jet pump performance are the diameters and lengths of the nozzle and throat, the geometry of the nozzle and throat inlets, and the distance between the nozzle exit and the throat inlet. (See, for example, the Kroll article previously cited.) It has been found, for the purposes of the present invention, that the two most critical parameters are nozzle diameter ($D_j$) and throat diameter ($D_t$), and the exercise of obtaining the results illustrated in FIG. 3 becomes one, therefore, of finding appropriate values for $D_j$ and $D_t$.

The first step in this exercise is that of determining the back pressure, $TP_d$, induced by the expiratory leg pneumatic resistance. A pressure-versus-flow rate graph can be easily generated experimentally for any given expiratory leg geometry. Such a graph might resemble the upper curve in FIG. 3. Then, the maximum expected flow rate $W_j$ for the system is determined, and, using this determined value of $W_j$, the expected value of $TP_d$ is determined from the aforementioned graph. (It should be noted that $W_j$ will not include any contribution from the patient's expiratory flow, since $TP_d$ is to be determined for the end of exhalation, when expiratory flow from the patient is, by definition, essentially zero.)

At this point, it is helpful to define some fluid-dynamic relationships that obtain in a jet pump. First, the area $A_j$ of the nozzle orifice may be defined by the following equation $$A_j = \frac{W_j T_1}{K P_1 N_{12} C}, \quad (1)$$

where $T_1$ is the total temperature upstream of the nozzle exit in degrees Rankin; $W_j$ is mass flow through the system, in pounds per second; K is a known constant for the gas, depending upon its composition, in units of $\sqrt{°R}$/second; $P_1$ is the total upstream pressure, in pounds per square inch; $N_{12}$ is a dimensionless factor which can be determined for any given gas in the manner explained below; and C is a coefficient of nozzle discharge. (See, for example, Anderson, *The Analysis and Design of Pneumatic Systems*, pp. 17-28, Robert E. Krieger Publishing Co., Huntington, New York, 1976).

As will be presently made clear, all of the above factors can be measured, calculated, or approximated to a sufficient degree of accuracy. For example, $T_1$ may be approximated as the measured ambient temperature. $W_j$ is determined empirically, as described above. K is known for any gas composition. C can be approximately as 0.95 for a well-rounded nozzle. $N_{12}$ is a function of the ratio of upstream pressure to downstream pressure for any given gas composition, and, under identical pressure conditions, is approximately the same for all diatomic gases, such as air and oxygen. Values of $N_{12}$ for diatomic gases have been tabulated and can be found, for example, in the previously cited Anderson reference, at pages 268-273.

$P_1$, the pressure upstream of the nozzle exit, may be approximated by the value of the total jet pressure $TP_j$, where $TP_j$ is defined as follows $$TP_j = \frac{(TP_d - TP_s)}{R_p} + TP_d, \quad (2)$$

where $TP_s$ is the desired net pressure in the chamber 22, and $R_p$ is an empirically-derived factor which is a function of nozzle area, throat area, and frictional flow resistance.

Using Equation 2, a value for $TP_j$ can be derived, once values for $TP_d$, $TP_s$, and $R_p$ are determined. The value for $TP_d$ is derived in the manner discussed above, while the desired value of $TP_s$ is atmospheric pressure. $R_p$ must be estimated. A family of curves has been empirically derived showing $R_p$ as a function of the ratio $R_a$ of nozzle area to throat area. See, for example, *Fan Engineering*, published by the Buffalo Forge Company (6th edition, 1961). The functional relationship between $R_p$ and $R_a$ varies as a function of the amount of pneumatic friction in the system. Hence discrete curves of $R_p$ versus $R_a$ have been generated for conditions of high, low, and moderate friction. It has been determined that for jet pumps in the size range of interest for the present purposes, the curve of $R_p$ versus $R_a$ for high friction conditions is the most accurate, and such a curve is shown in FIG. 4. From the curve of FIG. 4, it is seen that the maximum value of $R_p$ is approximately 0.5, and since $R_p$ remains reasonably close to this value over a relatively wide range of values of $R_a$, it is appropriate to use 0.5 as the value of $R_p$, at least for initial, gross calculations.

With $R_p$, $TP_d$, and $TP_s$ determined, $TP_j$ can be calculated. With the calculated value of $TP_j$ determined, $A_j$ can be calculated. Finally, using the relationship $R_a = A_j/A_t$ (where $A_t$ is the area of the throat 24), and the value of $R_a$ corresponding to the previously selected value of $R_p$ (from the curve of FIG. 4), the value of $A_t$ can be calculated. With the respective areas of the nozzle and throat so determined, it is a simple matter to determine their respective diameters.

By way of a specific example, assume that an expiratory leg geometry is selected such that at a maximum flow of 20 liters per minute (LPM), the back pressure generated at the throat is 4 centimeters of water (cmH2O) above atmospheric pressure. Since atmospheric pressure is 1034 cmH2O (14.70 psi), $TP_d$ has a value of 1038 cmH2O (14.81 psi). The desired value of $TP_s$ (which yields minimal inadvertent PEEP) is atmospheric pressure. As previously discussed, the value of $R_p$ is selected as 0.5. Thus, solving for $TP_j$ in Equation 2 we obtain:

$$TP_j = \frac{(1038 - 1034)}{0.5} + 1038$$

$$= 1046 \text{ cmH}_2\text{O} = 14.87 \text{ psi}.$$

Turning now to Equation 1 to solve for $A_j$, it has been established that $W_j = 20$ LPM $= 8.74 \times 10^{-4}$ pounds per second for air (since $W_j$ is a measure of mass flow, and air has a "mass" of $2.6 \times 10^{-3}$ lbs/liter). $T_1$ can be set at 530° R. (room temperature), K is $0.531 \sqrt{°R}$/second for air; and C is approximately 0.95, as discussed above. If upstream pressure is taken as the value of $TP_j$, and downstream pressure is taken as the value of $TP_s$, then the ratio of upstream to downstream pressure is:

$$\frac{1046 \text{ cmH}_2\text{O}}{1034 \text{ cmH}_2\text{O}} = 1.0116$$

From the tabulation of $N_{12}$ found in the above-cited Anderson reference, the value of $N_{12}$ for a pressure ratio of 1.0116 is 0.2198.

Inserting the values obtained above for $W_j$, $T_1$, K, C, and $N_{12}$ into Equation 1, along with the value of $P_1 = TP_j = 14.87$ psi obtained from Equation 2, the value of $A_j$ is calculated to be 0.0122 square inches, yielding a nozzle diameter $D_j$ of 0.124 inches.

Finally, using the relationship $R_a = A_j/A_t$, and taking the value of $R_a$ corresponding to $R_p = 0.5$ from the curve of FIG. 4, which value is seen to be approximately 0.3, $A_t$ is obtained as follows $A_t = A_j/R_a = 0.0122/0.3 = 0.0407$ inches, yielding a throat diameter $D_t$ of 0.227 inches.

From the foregoing, it can be seen that for any given expiratory leg geometry, yielding a value of $TP_d$ corresponding to a selected maximum flow rate, the nozzle and throat dimensions can be determined which will produce a pressure of approximately atmospheric level downstream of the nozzle at the end of the patient's exhalation, thus yielding, ideally, a PEEP value which is at or near zero. Moreover, with the nozzle and throat dimensions calculated at maximum flow rate, the minimal PEEP values will be obtained at all flow rates below the maximum.

It should be noted that, in actual practice, perfectly zero PEEP values will rarely be obtained inasmuch as the calculations used above make use of approximated values for several of the parameters. In addition, the actual dimensions of the jet pump orifices will be within tolerances, due to limitations in the manufacturing process.

Nevertheless, experiments with prototypes of the present invention have demonstrated substantially complete elimination of inadvertent PEEP. Thus, the principles upon which the invention is based, as discussed above, have proved valid, and it has been shown that dramatic reductions in inadvertent PEEP can be achieved, even with relatively unrefined approximations used in the calculations of the design parameters.

What is claimed is:

1. A ventilator of the type having an inspiratory flow path, an expiratory flow path, a patient adaptor connected therebetween and supply means for providing a substantially continuous flow of respiratory gas therethrough, said patient adaptor having an inlet fluidically connected to said inspiratory flow path, an outlet fluidically connected to said expiratory flow path, and patient connection means fluidically connected to said inlet and said outlet for fluidly coupling the patient adaptor to the breathing passages of a patient, wherein the improvement comprises:

a gas flow accelerating nozzle in said patient adaptor within said inlet such that substantially all gas flow through said inlet passes through said nozzle;

a chamber in said adaptor having an inlet opening and an outlet opening, said nozzle fluidly connected to said inlet opening, said chamber being in fluid communication with said patient connection means;

a throat in said adaptor downstream of said chamber and in alignment with said nozzle coupling said chamber outlet opening to said outlet;

said supply means providing said substantially continuous flow of gas within a range that would provide a depressed pressure in said chamber equal and opposite to a back pressure at said outlet opening caused by the pneumatic resistance of said continuous supply gas flow through said expiratory flow path when said expiratory flow from said patient through said adaptor is approximately zero so that the resulting pressure at said patient connection means is approximately equal to ambient pressure when gas is flowing from said inlet through said outlet at the end of the exhalation phase of said patient's respiratory cycle; and whereby said nozzle and said throat are internally dimensioned and said continuous flow of said supply means is selected such that said back pressure is substantially completely offset by the depressed pressure in said chamber created by the accelerated flow of gas through said nozzle.

* * * * *

UNITED STATES PATENT OFFICE
CERTIFICATE OF CORRECTION

Patent No. 4,417,573          Dated November 29, 1983

Inventor(s) Douglas F. De Vries

It is certified that error appears in the above-identified patent and that said Letters Patent are hereby corrected as shown below:

Column 2, line 64, "next" should read -- net --

Column 3, line 65, "wellknown" should read -- well-known --

Column 5, line 44-45, "approximately" should read -- approximated --

Column 6, line 49, "R." should read -- R --

Column 8, lines 24-30, "when said expiratory flow from said patient through said adaptor is approximately zero so that the resulting pressure at said patient connection means is approximately equal to ambient pressure when gas is flowing from said inlet through said outlet at the end of the exhalation phase of said patient's respiratory cycle " should be omitted in its entirety.

Signed and Sealed this

Twenty-first Day of February 1984

[SEAL]

Attest:

GERALD J. MOSSINGHOFF

Attesting Officer     Commissioner of Patents and Trademarks